United States Patent
Waugh et al.

(10) Patent No.: US 12,083,204 B2
(45) Date of Patent: Sep. 10, 2024

(54) TOPICAL COMPOSITION FOR HOMEOSTATIC DELIVERY OF NITRIC OXIDE AND USES THEREOF

(71) Applicants: L'OREAL, Paris (FR); Sisi Waugh, Las Vegas, NV (US)

(72) Inventors: Jacob Waugh, Las Vegas, NV (US); Jonah Shacknai, Santa Barbara, CA (US)

(73) Assignee: L'OREAL, Paris (FR)

( * ) Notice: Subject to any disclaimer, the term of this patent is extended or adjusted under 35 U.S.C. 154(b) by 56 days.

(21) Appl. No.: 17/831,333

(22) Filed: Jun. 2, 2022

(65) Prior Publication Data

US 2023/0390172 A1   Dec. 7, 2023

(51) Int. Cl.
*A61K 8/40* (2006.01)
*A61K 8/19* (2006.01)
(Continued)

(52) U.S. Cl.
CPC ............ *A61K 8/40* (2013.01); *A61K 8/19* (2013.01); *A61K 8/44* (2013.01); *A61K 8/4946* (2013.01);
(Continued)

(58) Field of Classification Search
None
See application file for complete search history.

(56) References Cited

U.S. PATENT DOCUMENTS 5,234,914 A   8/1993 Gallina
5,646,129 A   7/1997 Callegaro et al.
(Continued)

FOREIGN PATENT DOCUMENTS

BR   112013016950 A2   4/2020
CA         1341087 C   8/2000
(Continued)

OTHER PUBLICATIONS

Wessels et al., "The potential of a niacinamide dominated cosmeceutical formulation on fibroblast activity and wound healing in vitro", international wound journal ISSN 1742-4801, 2012, pp. 152-158. (Year: 2012).*

(Continued)

*Primary Examiner* — Kyung S Chang
(74) *Attorney, Agent, or Firm* — McNees Wallace & Nurick LLC

(57) ABSTRACT

Compositions that supplement and support nitric oxide availability to skin and methods of use include a first agent that is a precursor of nitric oxide, a second agent that facilitates production of nitric oxide by the first agent, and a third agent that antagonizes (i) nucleotide activation of skeletal muscle ryanodine receptors or (ii) cellular calcium influx. The first, second and third agents are mixed to form a composition suitable for topical application to skin. The composition may include an adenosine, arginine, carnosine, niacinamide, and a magnesium ion source, wherein application of the composition to a skin region increases cutaneous blood flow in the skin region compared to cutaneous blood flow in a similar skin region not treated with the composition, as measured by doppler ultrasound.

24 Claims, 5 Drawing Sheets
(1 of 5 Drawing Sheet(s) Filed in Color)

(51) Int. Cl.
  *A61K 8/44* (2006.01)
  *A61K 8/49* (2006.01)
  *A61K 8/60* (2006.01)
  *A61K 8/64* (2006.01)
  *A61K 8/67* (2006.01)
  *A61K 8/9789* (2017.01)
  *A61Q 19/08* (2006.01)

(52) U.S. Cl.
  CPC ............ *A61K 8/4953* (2013.01); *A61K 8/498* (2013.01); *A61K 8/606* (2013.01); *A61K 8/64* (2013.01); *A61K 8/675* (2013.01); *A61K 8/9789* (2017.08); *A61Q 19/08* (2013.01)

(56) References Cited

U.S. PATENT DOCUMENTS

| | | | |
|---|---|---|---|
| 5,895,658 | A | 4/1999 | Fossel |
| 6,271,216 | B1 | 8/2001 | Mello et al. |
| 6,809,075 | B1 | 10/2004 | Mitts et al. |
| 7,125,858 | B2 | 10/2006 | Filion et al. |
| 7,495,076 | B2 | 2/2009 | Gu et al. |
| 7,799,348 | B2 | 9/2010 | Ishaq |
| 8,324,356 | B2 | 12/2012 | Picotti et al. |
| 8,916,539 | B2 | 12/2014 | Yedgar et al. |
| 9,012,395 | B2 | 4/2015 | Calabro et al. |
| 9,050,336 | B2 | 6/2015 | Blanda et al. |
| 9,149,534 | B2 | 10/2015 | Leshshiner |
| 9,173,944 | B2 | 11/2015 | Taylor et al. |
| 9,561,255 | B2 | 2/2017 | Iwama et al. |
| 10,076,479 | B1 | 9/2018 | Santhanam et al. |
| 10,828,243 | B2 * | 11/2020 | Santhanam .......... A61K 8/9789 |
| 2001/0022975 | A1 | 9/2001 | Drizen et al. |
| 2001/0024658 | A1 | 9/2001 | Chen et al. |
| 2004/0019010 | A1 | 1/2004 | Karakelle et al. |
| 2004/0029970 | A1 | 2/2004 | Rask-Andersen et al. |
| 2004/0081672 | A1 | 4/2004 | Gupta |
| 2004/0219124 | A1 * | 11/2004 | Gupta .................. A61K 8/9767 424/70.13 |
| 2005/0048120 | A1 | 3/2005 | Edgren et al. |
| 2005/0054578 | A1 | 3/2005 | Sandberg et al. |
| 2005/0267068 | A1 | 12/2005 | Back et al. |
| 2006/0177483 | A1 | 8/2006 | Byrne et al. |
| 2006/0182794 | A1 | 8/2006 | Modi et al. |
| 2007/0020220 | A1 | 1/2007 | Osborne |
| 2007/0077292 | A1 | 4/2007 | Pinsky |
| 2007/0224150 | A1 | 9/2007 | Chung |
| 2008/0045909 | A1 | 2/2008 | Fossel |
| 2008/0050335 | A1 | 2/2008 | Faour et al. |
| 2008/0220021 | A1 | 9/2008 | Modi |
| 2009/0155314 | A1 | 6/2009 | Tezel et al. |
| 2009/0220415 | A1 | 9/2009 | Schachf et al. |
| 2009/0220497 | A1 | 9/2009 | Brown et al. |
| 2010/0068232 | A1 | 3/2010 | Key |
| 2010/0093686 | A1 | 4/2010 | Chappa et al. |
| 2010/0112016 | A1 | 5/2010 | Carli et al. |
| 2010/0124573 | A1 | 5/2010 | Naughton et al. |
| 2010/0135935 | A1 | 6/2010 | Leschiner et al. |
| 2010/0160849 | A1 | 6/2010 | Barbour |
| 2010/0172940 | A1 | 7/2010 | Petrella |
| 2010/0210585 | A1 | 8/2010 | Bresin et al. |
| 2010/0316724 | A1 | 12/2010 | Whitfield et al. |
| 2010/0317588 | A1 | 12/2010 | Shoseyov |
| 2011/0014241 | A1 | 1/2011 | Cohen |
| 2011/0033402 | A1 | 2/2011 | Modi |
| 2011/0033540 | A1 | 2/2011 | Daniloff et al. |
| 2011/0189239 | A1 | 8/2011 | Mansouri |
| 2011/0217249 | A1 | 9/2011 | Drehar |
| 2011/0245335 | A1 | 10/2011 | Prehm |
| 2012/0100194 | A1 | 4/2012 | Yamai et al. |
| 2012/0141397 | A1 | 6/2012 | Patel |
| 2012/0141532 | A1 | 6/2012 | Blanda et al. |
| 2012/0282591 | A1 | 11/2012 | Thatte et al. |
| 2013/0045290 | A1 | 2/2013 | Somerville |
| 2013/0059814 | A1 | 3/2013 | Chaumont et al. |
| 2013/0078294 | A1 | 3/2013 | Alexiades-Armenakas |
| 2013/0177505 | A1 | 7/2013 | Somerville et al. |
| 2013/0236571 | A1 | 9/2013 | Magdassi |
| 2014/0044797 | A1 | 2/2014 | Johansson et al. |
| 2014/0072613 | A1 | 3/2014 | Lander et al. |
| 2014/0228364 | A1 | 8/2014 | Hadj-Slimane |
| 2014/0236082 | A1 | 8/2014 | Roorda |
| 2014/0309157 | A1 | 10/2014 | Chung et al. |
| 2015/0132237 | A1 | 5/2015 | Leshchiner et al. |
| 2015/0157728 | A1 | 6/2015 | Modi |
| 2015/0182554 | A1 | 7/2015 | Koller et al. |
| 2015/0283045 | A1 | 10/2015 | Hack et al. |
| 2015/0342175 | A1 | 12/2015 | Suryan et al. |
| 2015/0374633 | A1 | 12/2015 | Fedorchak et al. |
| 2016/0000834 | A1 | 1/2016 | Kinsey et al. |
| 2016/0053029 | A1 | 2/2016 | Uha et al. |
| 2016/0089545 | A1 | 3/2016 | Uuluri et al. |
| 2016/0199498 | A1 | 7/2016 | Dai et al. |
| 2016/0324934 | A1 | 11/2016 | Angel et al. |
| 2017/0100523 | A1 | 4/2017 | Matheny |
| 2017/0189546 | A1 | 7/2017 | Bidwell, III et al. |
| 2017/0202769 | A1 | 7/2017 | Pilant |
| 2017/0216414 | A1 | 8/2017 | Tezel et al. |
| 2017/0266267 | A1 | 9/2017 | Osio |
| 2017/0290778 | A1 | 10/2017 | Waugh |
| 2019/0008795 | A1 | 1/2019 | Waugh |
| 2019/0105261 | A1 | 4/2019 | Waugh |
| 2019/0254948 | A1 | 8/2019 | Bader |
| 2020/0038314 | A1 | 2/2020 | Berge et al. |
| 2020/0368150 | A1 | 11/2020 | Damaj |
| 2021/0000910 | A1 | 1/2021 | Tan |
| 2021/0093539 | A1 * | 4/2021 | LaRosa .................. A61K 8/416 |
| 2021/0137810 | A1 | 5/2021 | Stasko et al. |
| 2021/0290737 | A1 | 9/2021 | Cappello |
| 2021/0369596 | A1 | 12/2021 | Carle et al. |

FOREIGN PATENT DOCUMENTS

| | | | |
|---|---|---|---|
| CA | 2494473 | A1 | 4/2005 |
| CA | 2761740 | A1 | 11/2010 |
| CA | 2703532 | A1 | 11/2011 |
| CH | 705713 | B1 | 5/2013 |
| CH | 711092 | A | 5/2015 |
| CN | 104721116 | A | 6/2015 |
| CN | 105213298 | A | 1/2016 |
| CN | 112386520 | A * | 2/2021 |
| EP | 2567689 | A1 | 3/2013 |
| EP | 2922581 | B1 | 3/2017 |
| FR | 2877574 | A1 | 5/2006 |
| FR | 2971711 | A1 | 8/2012 |
| FR | 3024660 | A1 | 2/2016 |
| JP | H07101831 | A | 4/1995 |
| JP | 2001-139447 | A | 5/2001 |
| KR | 102248733 | B1 | 5/2021 |
| KR | 20210078713 | A | 6/2021 |
| TW | M622532 | U | 1/2022 |
| WO | WO 2002/051380 | A1 | 7/2002 |
| WO | WO 2007/021970 | A2 | 2/2007 |
| WO | WO 2007/041627 | A1 | 4/2007 |
| WO | WO 2008/003321 | A2 | 1/2008 |
| WO | WO 2008/124169 | A2 | 10/2008 |
| WO | WO 2010/009809 | A2 | 1/2010 |
| WO | WO 2010/135527 | A2 | 11/2010 |
| WO | WO 2014/044808 | A2 | 3/2014 |
| WO | WO 2014/086679 | A1 | 6/2014 |
| WO | WO 2014/134523 | A1 | 9/2014 |
| WO | WO 2015/017601 | A2 | 2/2015 |
| WO | WO 2016/112051 | A1 | 7/2016 |
| WO | WO 2016/207340 | A1 | 12/2016 |
| WO | WO 2017/180788 | A1 | 10/2017 |

OTHER PUBLICATIONS

CN-112386520-A Google English Translation (Year: 2020).*
Albericio and Kruger, "Therapeutic peptides", Future Medicinal Chemistry, vol. 4, No. 12, pp. 1527-1531 (2012).
Bentov et al. "The effect of aging on the cutaneous microvasculature", Microvasc. Res., vol. 100, pp. 25-31 (2015).

(56) References Cited

OTHER PUBLICATIONS

Bruch-Gerharz et al., "Nitric oxide in human skin: current status and future prospects", J. Invest. Dermatol., vol. 110, No., 1, pp. 1-7 (1998).

Czech et al., "Collagen Peptides—Source, Properties, and Benefits", Seagarden AS, Online article downaloded from www.seagarden.no, 7 pages (2016).

Essendoubi et al., "Human skin penetration of hyaluronic acid of different molecular weights as probed by Raman spectroscopy", Skin Res. Tech., pp. 1-8 (2015).

Gad, "Anti-aging effects of l-arginine", J. Adv. Res., vol. 1, Issue 3, pp. 169-177 (2010).

Gura, "Systems for identifying new drugs are often faulty", Science, vol. 278, No. 5340, pp. 1041-1042 (1997).

Habibi et al., "Self-assembled peptide-based nanostructures: Smart nanomaterials toward targeted drug delivery", Nano Today, vol. 11, No. 1, pp. 41-60 (2016).

International Search Report and Written Opinion from International Application No. PCT/US2017/27275, 8 pages, mailed Jul. 14, 2017.

International Search Report and Written Opinion from International Application No. PCT/US2018/055499, 9 pages, mailed Dec. 27, 2018.

Kim et al. "Age-related changes in skin bio-mechanical properties: the neck skin compared with the cheek and forearm skin in Korean females", Skin Res. Technol., vol. 19, No. 3, pp. 236-241 (2013).

Laver et al., "Regulation of the calcium release channel from rabbit skeletal muscle by the nucleotides ATP, AMP, IMP and adenosine", J. Phys., vol. 537, No. 3, pp. 763-778 (2001).

Laver, "Coupled calcium release channels and their regulation by luminal and cytosolic ions", Eur. Biophys. J., vol. 34, pp. 359-368 (2005).

Martins et al., "Design of Novel BSA/Hyaluronic Acid Nanodispersions for Transdermal Pharma Purposes," Molecular Pharmaceutics, vol. 11, pp. 1479-1488 (2014).

Mirza and Khatri, ", The use of lasers in the treatment of skin cancer: A review", J. Cosmetic and Laser Therapy, vol. 19, No. 8, pp. 451-458 (2017).

Murayama et al., "Role of Mg21 in Ca21-Induced Ca21 Release through Ryanodine Receptors of Frog Skeletal Muscle: Modulations by Adenine Nucleotides and Caffeine", Biophysical J., vol. 78, pp. 1810-1824 (2000).

Ryan et al., "The ageing of the blood supply and the lymphatic drainage of the skin", Micron., vol. 35, No. 3, pp. 161-171 (2004).

Samy et al., "Novel microstructured sildenafil dosage forms as wound healing promoters", Expert Opinion on Drug Delivery, vol. 11, No. 10, pp. 1525-1536 (2014).

Shrewsbury, Applied Pharmaceutics in Contemporary Compounding, Chapter 17, pp. 229-230 (2015).

Takahashi et al., "Carnosine Facilitates Nitric Oxide Production in Endothelial F-2 Cells", Biol. Pharm. Bull., vol. 31, No. 11, pp. 1836-1839 (2009).

Tecno™ Neck Perfecting Cream, Promotional Brochure, Skinbetter Science, Phoenix, AZ 85018, 16 pages (2021).

Tripodo et al., "Hyaluronic acid and its derivatives in drug delivery and imaging: Recent advances and challenges", European J. Pharm. Biopharm., vol. 97, pp. 400-416 (2015).

Xie et al., "Hyaluronic Acid: Evaluation as a Potential Delivery Vehicle for Vitronectin: Growth Factor Complexes in Would Healing Applications" *Authors version submitted/accepted for publication in*, Journal of Controlled Release, vol. 153 pp. 225-232 (2011), Downloaded from: http://eprints.qut.edu.au/46400/.

Yang et al., "Transdermal delivery of hyaluronic acid—Human growth hormone conjugate" Biomaterials, vol. 33, pp. 5947-5954 (2012).

Zhang et al., "Cosmetics and peptides", Clinics in Dermatology, vol. 27, pp. 485-494 (2009).

Anonymous, Mintel, "Daily Tone Up Sun Block SPF50+ Pa++++," Record ID 6602251, Jun. 2019, www.gnpd.com.

Anonymous, Mintel, "Sheer Cream," Record ID 5925293, Aug. 2018, www.gnpd.com.

Anonymous, Mintel, "Sym-Micro Essence," Record ID 7607177, May 2020, www.gnpd.com.

Anonymous, Mintel, "Night Line Smoothing Cream for Combination Oily to Oily Skin," Feb. 15, 2015, XP093074343.

Notification of Transmittal of the International Search Report and the Written Opinion of the International Searching Authority, or the Declaration issued to counterpart Application No. PCT/IB2023/055709 dated Mar. 6, 2024.

\* cited by examiner

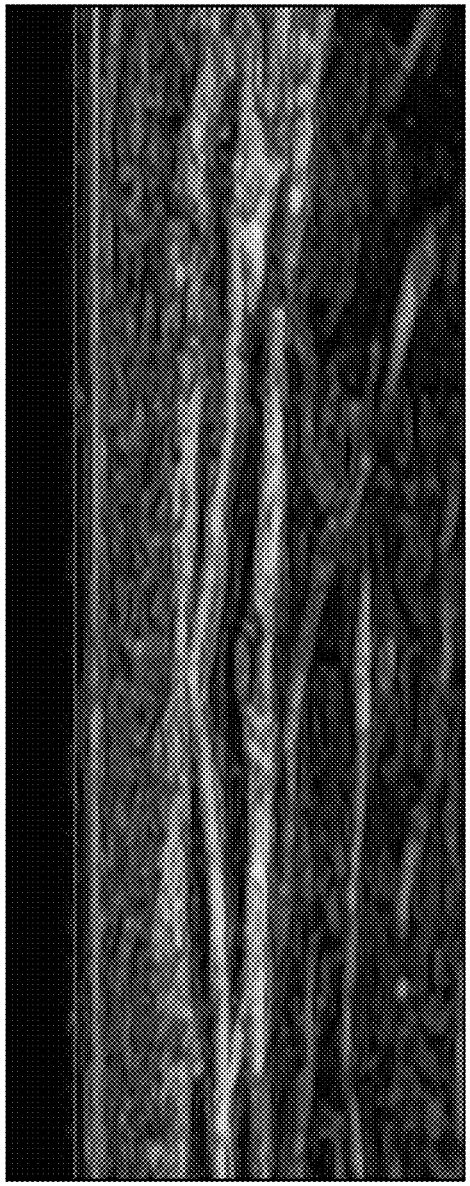
FIG. 3A
Untreated Control
FIG. 3B
2.5 hrs post application of Composition T-1
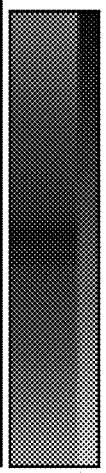
Visual change in blood flow

TOPICAL COMPOSITION FOR HOMEOSTATIC DELIVERY OF NITRIC OXIDE AND USES THEREOF

CROSS-REFERENCE TO RELATED APPLICATIONS

This field intentionally left blank.

TECHNICAL FIELD

The subject matter described herein relates to topical compositions that supplement and support availability of nitric oxide to skin and uses thereof.

BACKGROUND

The skin is the largest organ of the human body. Unfortunately, skin diseases and undesirable skin conditions are common and, according to studies, affect as many as one in three Americans at any given time. Treatment of conditions of the skin is important for both overall health, but also for appearance, the latter being associated with self-esteem and other important aspects of mental health. Common treatment methods for skin conditions include medicated creams and ointments, including agents such as antibiotics, antioxidants, retinoids, alpha hydroxy acids, peptides, and vitamins. Surveys indicate that the average American spends over $300 per year on skincare, possibly resulting in expenditures of more than $15,000 over a lifetime. The overall global market for skin care products is over 145.3 billion dollars per year.

A skin area may be a person's neck, décolleté, face, and/or back of hands. Compared to skin on the face, neck skin is thinner, more extensible, and subject to constant movement. Also, neck skin is highly exposed to environmental insults, and often neglected. Neck skin shows a more severe aging pattern including deeper wrinkles, skin sagging and laxity than other skin areas, and experiences suboptimal oxygen and nutrients. Due to having fewer sebaceous glands than the face, neck has an increasing need for moisturization support. As such, the neck area benefits most from a targeted skincare solution.

Nitric oxide plays a role in helping maintain homeostasis and balance in all cells of the body, including skin cells. Nitric oxide dilates blood vessels and increases blood flow. It contributes to vessel homeostasis by inhibiting vascular smooth muscle contraction. Nitric oxide stimulants induce formation of cyclic guanosine monophosphate (cGMP) in the vascular smooth muscle cells and through a series of activations (PKG) prevent the calcium influx, ultimately resulting in smooth muscle relaxation.

Youthful-acting skin cells require nitric oxide to open up nutrient and oxygen channels in the skin. The flow of nutrients and oxygen to skin cells is critical to dermal health and the body's natural healing process. Aging is associated with deficits in nitric oxide availability, contributing to a 40% reduction in blood flow to the skin between the ages of 20 to 70 years. Reduction in nitric oxide contributes to signs of skin aging such as fine lines and wrinkles, crepiness, hyperpigmentation and dryness. As a result, cells function less efficiently, making them more vulnerable to accelerated skin aging (Eunjoo K, et al. *Skin Res and Technol.* 2013 August; 19(3):236-41; Ryan T, et al. *Micron.* 2004; 35(3):161-71; Bruch-Gerharz D. *J Invest Dermatol.* 1998 January; 110(1):1-7; Gad M Z. *J Adv Res.* 2010; 1:169-177; Bentov I, et al. *Microvasc Res.* 2015 July; 100:25-31).

BRIEF SUMMARY

The present disclosure provides topical compositions/skincare products that supplement and support nitric oxide availability to skin. The following aspects and embodiments thereof described and illustrated below are meant to be exemplary and illustrative, not limiting in scope.

In one aspect, the present disclosure provides a composition comprising a first agent that is a precursor of nitric oxide, a second agent that facilitates production of nitric oxide by the first agent, and a third agent that antagonizes (i) nucleotide activation of skeletal muscle ryanodine receptors or (ii) cellular calcium influx. The first, second and third agents are mixed to form a composition suitable for topical application to skin.

In some embodiments, the first agent may be selected from the group consisting of arginine, citrulline, nitroglycerin, amyl nitrite, and sildenafil. In certain embodiments, the first agent may be L-arginine. By way of non-limiting example, L-arginine is present in the composition in an amount of about 0.1-1 wt %.

In some embodiments, the second agent may be niacinamide, carnosine, or both. In certain embodiments, the composition may comprise about 1.5-6 wt % niacinamide and/or about 0.05-0.2 wt % carnosine.

In some embodiments, the third agent may antagonize nucleotide activation of skeletal muscle ryanodine receptors. In certain embodiments, the third agent may be adenosine. By way of non-limiting example, the composition may comprise about 0.01-0.5 wt % adenosine.

In some embodiments, the third agent may antagonize cellular calcium influx. In certain embodiments, the third agent may be a source of magnesium. In certain embodiments, the source of magnesium may be a magnesium salt. By way of non-limiting example, the magnesium salt may be magnesium gluconate, magnesium glycinate, magnesium citrate, magnesium carbonate, magnesium malate, magnesium taurate, magnesium hydroxide, magnesium sulfate, magnesium hydroxide, or magnesium oxide. In certain embodiments, the composition may comprise about 0.1-1 wt %, 0.4-0.8 wt % or 0.4-0.6 wt % of a magnesium source or magnesium ion source.

In some embodiments, any one of the compositions disclosed above and herein may further comprise an extracellular matrix component. In certain embodiments, the extracellular matrix component may be collagen, elastin, fibronectin, hyaluronic acid or lectin. In certain embodiments, the extracellular matrix component has an average molecular weight of about 1,000-60,000 daltons, or about 1,000-40,000 daltons, or about 1,000-30,000 daltons, or about 1,000-25,000 daltons, or about 1,000-20,000 daltons, or about 1,000-15,000 daltons, or about 1,000-10,000 daltons.

In some embodiments, any one of the compositions described above and herein may further comprise a cosmeceutically acceptable vehicle.

In some embodiments, any one of the compositions described above and herein may be an emulsion. In certain embodiments, the emulsion may be an oil-in-water emulsion.

In another aspect, the present disclosure provides a composition comprising an adenosine, arginine, carnosine, niacinamide, and a magnesium ion source. Application of the composition to a skin region increases cutaneous blood flow in the skin region compared to cutaneous blood flow in a similar skin region not treated with the composition, as measured by doppler ultrasound.

In some embodiments, the ratio of arginine to adenosine in the composition may be between about 10:1 and about 100:1. By way of non-limiting example, the ratio of arginine to adenosine is about 25:1.

In some embodiments, the ratio of arginine to carnosine may be between about 2:1 and about 20:1. By way of non-limiting example, the ratio of arginine to carnosine is about 5:1. In some specific examples, the ratio of arginine to carnosine is about 5:1 and the ratio of arginine to adenosine is about 25:1 in the composition.

In some embodiments, the composition may comprise about 0.1-1 wt % arginine, about 0.01-0.06 wt % adenosine, about 0.05-0.2 wt % carnosine, and/or about 0.5-6 wt % niacinamide.

In some embodiments, the composition described above and herein may further comprise an extracellular matrix component selected from the group consisting of collagen, elastin, hyaluronic acid, and sodium hyaluronate. In certain embodiments, the sodium hyaluronate may be hydrolyzed sodium hyaluronate.

In some embodiments, the composition may further comprise an antioxidant. Any gallate type or catechin type antioxidant can be used. By way of non-limiting example, in an embodiment, the antioxidant is epigallocatechin gallate (i.e., an antioxidant most commonly derived from green tea).

In some embodiments, arginine may be L-arginine.

In some embodiments, a magnesium ion source may be a magnesium salt. In certain embodiments, the magnesium salt may be selected from the group consisting of magnesium gluconate, magnesium glycinate, magnesium citrate, magnesium carbonate, magnesium malate, magnesium taurate, magnesium hydroxide, magnesium sulfate, magnesium hydroxide, and magnesium oxide.

In some embodiments, the composition described above and herein may further comprise an extra cellular matrix component. In certain embodiments, the extracellular matrix component may be selected from the group consisting of collagen, elastin, fibronectin, hyaluronic acid and lectin. In certain embodiments, the extracellular matrix component has an average molecular weight of about 1,000-60,000 daltons, or about 1,000-40,000 daltons, or about 1,000-30,000 daltons, or about 1,000-25,000 daltons, or about 1,000-20,000 daltons, or about 1,000-15,000 daltons, or about 1,000-10,000 daltons.

In still another aspect, the present disclosure provides a composition comprising arginine, carnosine, an adenosine, a skin firming agent, a skin hydration agent, a skin barrier agent, and an antioxidant.

In some embodiments, the ratio of arginine to carnosine is about 5:1 and the ratio of arginine to adenosine is about 25:1 in the composition.

In some embodiments, the ratio of arginine to adenosine is between about 10:1 and about 100:1 or between about 15:1 and about 50:1 in the composition.

In some embodiments, the ratio of arginine to carnosine is between about 2:1 and about in the composition. In certain embodiments, the ratio of arginine to carnosine is between about 2:1 about 10:1 in the composition.

In some embodiments, the composition may comprise about 0.1-1 wt % arginine, about wt % adenosine, and/or about 0.05-0.2 wt % carnosine.

In some embodiments, the skin firming agent comprised in the composition described above and herein may be selected from the group consisting of heptapeptide-7, magnesium gluconate, *Nicotiana benthamiana* hexapeptide-40sh-polypeptide-76, and hydrolyzed *Eragrostis tef* seed extract.

In some embodiments, the skin hydration agent may be selected from the group consisting of fruit extract complex, hydrolyzed sodium hyaluronate, niacinamide, and jojoba esters.

In some embodiments, the skin barrier agent may be selected from the group consisting of jojoba esters, linoleic acid, linolenic acid, and squalane.

In some embodiments, the antioxidant may be selected from the group consisting of tocopheryl acetate, aminopropyl ascorbyl phosphate, and epigallocatechin gallate.

In yet another aspect, the present disclosure provides a method for treating skin. Such method comprises providing any one of the compositions described above and herein, and applying or instructing to apply the composition to skin.

In some embodiments, the composition may be applied to the skin once daily or twice daily. In some embodiments, the composition may be applied to the skin for a period of at least about 2 weeks or at least about 1 month. In some embodiments, the composition is applied to skin on a person's neck, décolleté, face, and/or back of hands.

In any of the methods described above and herein, applying the composition to skin achieves a beneficial change in the skin. In certain embodiments, the beneficial change may be one or more of the following: a reduced appearance of fine lines or fine wrinkles, an improved appearance of sun damage, an improved appearance of skin firmness, an improved skin appearance, a perceived improvement in skin appearance, an improved evenness in skin tone, an improved hydration of skin, a reduction in redness, and/or an improved skin tone.

In any of the methods described above and herein, nitric oxide is produced or generated after application of the composition to skin, as evidenced by one or more of the following: an increased cutaneous blood flow in the treated skin region compared to cutaneous blood flow in a similar skin region not treated with the composition; an increased cutaneous blood flow in the treated skin region compared to cutaneous blood flow in a similar skin region treated with a composition identical in all respects except for the absence of one or more of arginine, adenosine, and/or carnosine; and/or an increased cutaneous blood flow in the treated skin region for a period of about 2-48 hours after application to skin.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3B illustrate evaluation of cutaneous blood flow in the neck skin between baseline (untreated control; FIG. 3A) and 2.5 hours following application of the exemplary topical composition T-1 (FIG. 3B).

DETAILED DESCRIPTION

Figure 1:
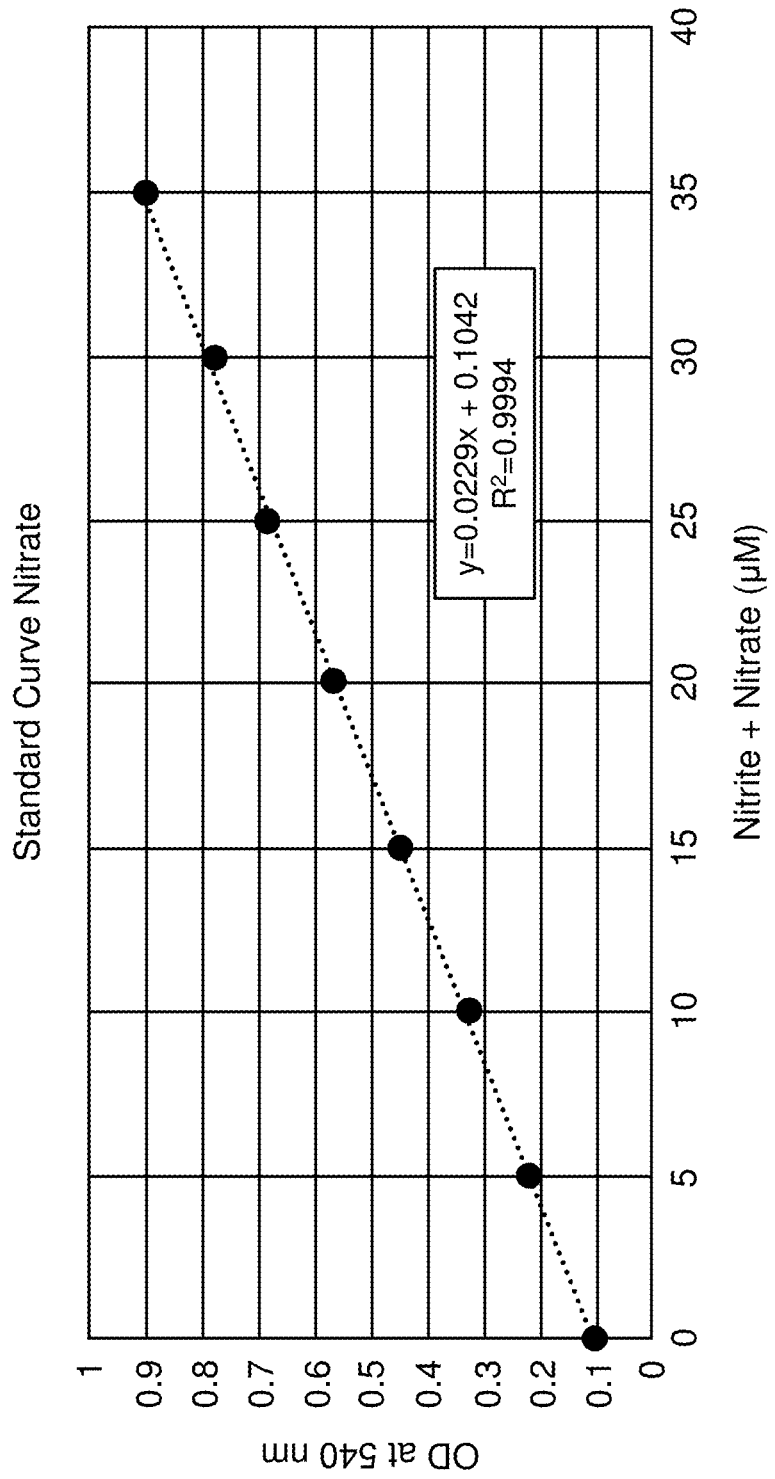
FIG. 1 is a standard curve used to determine the concentration of test proteins.

Levels of natural nitric oxide in the body decline as skin ages or is damaged by environmental stressors, the time when skin cells need access to nitric oxide the most. The present disclosure provides a targeted solution that supplements and supports nitric oxide availability to draw from and addresses skin aging and damage. With this target solution, nitric oxide is ready for access and deployment to skin when needed. That is, nitric oxide is made available on demand as the skin needs it to achieve balance.

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "active agent" is used herein to refer to a chemical material or compound that induces a desired beneficial effect when administered topically or subcutaneously, and includes agents that are therapeutically and/or prophylactically effective as pharmaceuticals ("pharmacologically active agents"), as well as agents that are cosmeceutically effective ("cosmeceutically active agents"). Also included are derivatives and analogs of those compounds or classes of compounds specifically mentioned that also induce the desired effect. By an "effective" amount of an active agent is meant a nontoxic but sufficient amount of an active agent to provide the desired beneficial effect. More specifically, by a "therapeutically effective," "prophylactically effective," or "cosmeceutically effective" amount is meant a nontoxic but sufficient amount of a beneficial agent to provide the desired therapeutic, prophylactic, or cosmeceutical effect.

The term "aging-related skin condition" relates to any skin condition or disorder associated with, caused by, or affected by, intrinsic aging and/or extrinsic aging. Aging-related skin conditions that may be treated using the present methods and formulations include, but are not limited to, wrinkles, age spots, sun damage (particularly UV radiation-induced oxidative stress), blemishes, hyperpigmented skin, age spots, increased skin thickness, loss of skin elasticity and collagen content, dry skin, lentigines, melasmas, as well as scars.

The terms "buffer" or "buffering agents" refer to materials which when added to a solution, cause the solution to resist changes in pH.

"Carriers" or "vehicles" as used herein refer to carrier materials suitable for incorporation in a topically or subcutaneously applied composition. Carriers and vehicles useful herein include any such materials known in the art, which are nontoxic and do not interact with other components of the formulation in which it is contained in a deleterious manner.

The terms "chelator" or "chelating agent" refer to any materials having more than one atom with a lone pair of electrons that are available to bond to a metal ion.

By "cosmeceutically effective" and "cosmetic effect" is meant a nontoxic agent that when applied to the surface of skin beneficially affects and/or changes the appearance of the skin, e.g., reducing fine lines and wrinkles of the skin, without changing the structure of skin.

The terms "cosmeceutically active agent" and "cosmeceutically active base" are used interchangeably herein to refer to a cosmeceutically effective basic compound or composition of matter which, when topically administered to a human patient, is effective to treat one or more aging-related skin conditions. Also included are derivatives and analogs of those compounds or classes of compounds that also induce the desired effect, e.g., an application for improving the appearance of an aging-related skin condition.

The terms "treating" and "treatment" as used herein refer to reduction in severity and/or elimination of skin related conditions resulting from intrinsic and/or extrinsic aging processes of the skin, or other trauma to the skin resulting in, e.g., a scar. The present method of "treating" a skin condition related to aging, as the term is used herein, refers to the prevention of aging-related skin conditions as well as the treatment of aging-related skin conditions in affected individuals. That is, the present method of "treating" includes improving the appearance of or mitigating the onset of future damage to skin, and/or improving the structure and function of skin. Aging-related skin conditions include, but are not limited to, photodamage, pigmentation, wrinkles, fine lines.

By "cosmeceutically acceptable," such as in the recitation of a "cosmeceutically acceptable carrier," or a "cosmeceutically acceptable derivative," is meant a compound that is not biologically or otherwise undesirable, i.e., the compound may be incorporated into a cosmeceutical formulation and topically administered to a patient without causing any undesirable biological effects or interacting in a deleterious manner with any of the other components of the cosmeceutical formulation in which it is contained. The term "pharmaceutically acceptable" is used in an analogous manner, to refer to a compound or composition that may be incorporated into a pharmaceutical formulation herein (i.e., a formulation containing one or more pharmacologically active agents) without causing undesirable biological effects or unwanted interaction with other components of the formulation.

The term "stable" as in a stable emulsion means that the composition retains its structure as an emulsion. A desired emulsion structure, for example, may be characterized by a desired size range, macroscopic observations of emulsion science (is there one or more layers visible, is there visible precipitate), pH, and a stable concentration of one or more the components.

The term "subject" as used herein refers to organisms to be treated by the compositions. Such organisms include animals (domesticated animal species, wild animals), and humans.

The term "surfactant" refers to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group.

As used herein, the term "topically" refers to application of the compositions to the surface of the skin and tissues.

The compositions of the present disclosure can comprise, consist essentially of, or consist of, the components disclosed.

All percentages, parts and ratios are based upon the total weight of the topical compositions and all measurements made are at about 25° C., unless otherwise specified.

By reserving the right to proviso out or exclude any individual members of any such group, including any subranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

II. Compositions

Compositions that supplement and support nitric oxide availability to skin (e.g., neck or décolleté skin) are provided herein. The compositions generate nitric oxide in situ after topical application to the skin, providing nitric oxide locally in the skin and in response to the local skin environment. The compositions harness the power of the body's natural process of nitric oxide creation to visibly improve aging skin. Upon application of these compositions to skin, one or more of the following effects are achieved: skin looked firmer and more resilient; the appearance of crepiness, laxity and texture improved; and/or skin was intensely hydrated thus the suppleness of the skin improved.

In one aspect, the present disclosure provides a composition comprising a first agent that is a precursor of nitric oxide, a second agent that facilitates production of nitric oxide by the first agent, and a third agent that antagonizes (i) nucleotide activation of skeletal muscle ryanodine receptors or (ii) cellular calcium influx. The first, second and third agents are mixed to form a composition suitable for topical application to skin. The composition may further comprise stabilizing ingredients.

The agent that is a precursor of nitric oxide may be arginine, citrulline, nitroglycerin, amyl nitrite, and/or sildenafil. In an embodiment, the nitric oxide precursor is present in the composition in an amount of between about 0.05-2 wt %, 0.075-1.5 wt %, 0.1-1.5 wt %, 0.1-1.25 wt %, 0.1-1 wt %, 0.2-0.8 wt % or 0.3-0.6 wt %. In an embodiment, the first agent is L-arginine, which is a natural ingredient that metabolizes to nitric oxide. It can be processed by the skin and deployed as nitric oxide, on demand and as needed, when delivered to the skin in a composition as detailed herein, where the precursor is stable in the composition (e.g., as evidenced by minimal degradation of the precursor when stored at room temperature for 6 months or 12 months), and where complimentary ingredients in the composition facilitate its penetration through the stratum corneum and into the epidermal and/or dermal layers.

Nitric oxide is a signaling molecule and functions to dilate blood vessels. The precursor of nitric oxide is instrumental in generation of nitric oxide in the skin, and also facilitates migration of the other ingredients in the composition into the skin, at least in part by dilation of blood vessels. In addition, the precursor of nitric oxide is capable of stimulating the cells to produce proteins, such as collagen and elastin, which facilitates the beneficial change in the skin achieved by the composition.

The composition, in an embodiment, also comprises an agent that facilitates activation of nitric oxide. Exemplary agents include niacinamide and/or carnosine. For instance, the composition may comprise between about 0.5-6 wt %, 1-6 wt %, 1.5-6 wt %, 1.5-5 wt %, 2-5 wt %, 2-4 wt %, 2.5-4.5 wt %, or 2.5-3.5 wt % niacinamide and/or between about 0.05-0.2 wt %, 0.08-0.2 wt %, 0.09-0.2 wt %, 0.075-0.15 wt %, 0.08-0.15 wt %, 0.09-0.15 wt %, 0.09-0.125 wt % carnosine. Niacinamide (nicotinamide) plays a role in the arginine conversion to nitric oxide via NADPH (reduced nicotinamide adenine dinucleotide phosphate). Carnosine facilitates nitric oxide (NO) production via endothelial NO synthase (eNOS) activated by released from intracellular $Ca^{2+}$ pathway.

As used herein, the term "carnosine" includes and encompasses the di-peptides beta-alanyl-histidine and all related compounds such as anserine (beta-alanyl-1-methyl-histidine) and homocarnosine (gamma-amino-butyryl-histidine). As used herein, the term "carnosine" also includes D, L-carnosine, D-carnosine, L-carnosine, as well as salts thereof and modified carnosine.

The third agent may antagonize nucleotide activation of skeletal muscle ryanodine receptors. An example of the third agent is adenosine. By way of non-limiting example, the composition may comprise adenosine in any of the ranges mentioned above. Adenosine acts as a competitive antagonist that reversibly inhibited ATP- and AMP-activated ryanodine receptors (RyRs).

Alternatively, the third agent may antagonize cellular calcium influx. An example of such an agent is a source of magnesium, e.g., a magnesium salt. Magnesium acts as competitive antagonists for the $Ca^{2+}$ influx channel, inhibiting muscle contraction. By way of non-limiting example, the magnesium salt may be magnesium gluconate, magnesium glycinate, magnesium citrate, magnesium carbonate, magnesium malate, magnesium taurate, magnesium hydroxide, magnesium sulfate, magnesium hydroxide, or magnesium oxide. In certain embodiments, the composition may comprise about 0.1-1 wt %, 0.2-1 wt %, 0.3-0.9 wt %, 0.4-0.8 wt %, or 0.4-0.6 wt % of a source of magnesium or a source of magnesium ion.

Any one of the compositions disclosed above and herein may further comprise an extracellular matrix component. The extracellular matrix may be selected from the group consisting of collagen, elastin, fibronectin, hyaluronic acid, sodium hyaluronate (e.g., hydrolyzed sodium hyaluronate), and lectin. In certain embodiments, the extracellular matrix component has an average molecular weight of about 1,000-60,000 daltons, or about 1,000-40,000 daltons, or about 1,000-30,000 daltons, or about 1,000-25,000 daltons, or about 1,000-20,000 daltons, or about 1,000-15,000 daltons, or about 1,000-10,000 daltons.

Any one of the compositions described above and herein may further comprise a cosmeceutically acceptable vehicle. The vehicle or carrier may be incorporated into a cosmeceutical formulation of the present disclosure and topically administered to a patient without causing any undesirable biological effects or interacting in a deleterious manner with any of the other components of the cosmeceutical formulation in which it is contained.

Any one of the compositions described above and herein may be an emulsion. In exemplary embodiments, the emulsion may be an oil-in-water emulsion.

In another aspect, the present disclosure provides a composition comprising an adenosine, arginine (e.g., L-arginine), carnosine, niacinamide, and a magnesium ion source. Application of the composition to a skin region increases cutaneous blood flow in the skin region compared to cutaneous blood flow in a similar skin region not treated with the composition, as measured by doppler ultrasound.

In some embodiments, the composition may comprise between about 0.1-1 wt % arginine, between about 0.01-0.06 wt % adenosine, between about 0.05-0.2 wt % carnosine, and/or between about 1.5-6 wt % niacinamide. In some embodiments, the ratio of arginine to adenosine in the composition may be between about 10:1 and about 100:1, e.g., the ratio of arginine to adenosine is about 25:1. In some embodiments, the ratio of arginine to carnosine may be between about 2:1 and about 20:1, e.g., the ratio of arginine to carnosine is about 5:1. In exemplary embodiments, the ratio of arginine to carnosine is about 5:1 and the ratio of arginine to adenosine is about 25:1 in the composition.

The compositions described above and herein may further comprise an antioxidant, such as epigallocatechin gallate (i.e., green tea antioxidant).

A magnesium ion source may be a magnesium salt selected from the group consisting of magnesium gluconate, magnesium glycinate, magnesium citrate, magnesium carbonate, magnesium malate, magnesium taurate, magnesium hydroxide, magnesium sulfate, magnesium hydroxide, and magnesium oxide. Such magnesium ion source antagonizes cellular calcium influx.

In still another aspect, the present disclosure provides a composition comprising arginine, carnosine, an adenosine, a skin firming agent, a skin hydration agent, a skin barrier agent, and an antioxidant. In some embodiments, the ratio of arginine to carnosine is about 5:1 and the ratio of arginine to adenosine is about 25:1 in the composition. In some embodiments, the ratio of arginine to adenosine is between about 10:1 and about 100:1 or between about 15:1 and about 50:1 in the composition. In some embodiments, the ratio of arginine to carnosine is between about 2:1 and about 20:1 in the composition. In certain embodiments, the ratio of arginine to carnosine is between about 2:1 about 10:1 in the composition.

In some embodiments, the composition may comprise about 0.1-1 wt % arginine, about 0.01-0.06 wt % adenosine, and/or about 0.05-0.2 wt % carnosine. The combination of these agents, along with stabilizing ingredients, facilitates nitric oxide production when applied to skin and support nitric oxide availability to the skin.

The skin firming agent comprised in the composition disclosed above and herein may be selected from the group consisting of heptapeptide-7, magnesium gluconate, *Nicotiana benthamiana* hexapeptide-40sh-polypeptide-76, and hydrolyzed *Eragrostis tef* seed extract. heptapeptide-7 is a targeted peptide that supports the extracellular matrix (ECM). Magnesium gluconate is skin-supporting mineral that helps soften and reduce the appearance of expression lines and wrinkles. *Nicotiana benthamiana* hexapeptide-40sh-polypeptide-76 is a plant-derived growth factor that helps to smooth the appearance of wrinkles and texture, enhancing the appearance of skin radiance. Hydrolyzed *Eragrostis tef* seed extract is a superfood extract that helps support collagen, resulting in an improvement in the appearance of neck lines, creating smoother and firmer-looking skin.

The skin hydration agent comprised in the composition disclosed above and herein may be selected from the group consisting of fruit extract complex, hydrolyzed sodium hyaluronate, niacinamide, and jojoba esters. Fruit extract complex hydrates the skin by supporting key Natural Moisturizing Factor (NMF) components such as sodium lactate, sodium PCA and citrulline. Hydrolyzed sodium hyaluronate helps provide skin with high moisture retention and free-radical defense. Niacinamide is a moisturizing source of Vitamin B3. Jojoba esters provides hydration and supports the skin's barrier. That is, jojoba esters is both a skin hydration agent and a skin barrier agent.

The skin barrier agent comprised in the composition disclosed above and herein may be selected from the group consisting of jojoba esters, linoleic acid, linolenic acid, and squalane. Linoleic and linolenic acids are essential fatty acids that support the skin's barrier (Omega-6 and Omega-3). Squalane is a naturally occurring emollient in the skin that supports moisture retention to improve skin suppleness and flexibility.

The antioxidant comprised in the composition disclosed above and herein may be selected from the group consisting of tocopheryl acetate, aminopropyl ascorbyl phosphate, and epigallocatechin gallate (EGCG). Tocopheryl acetate is a form of Vitamin E that provides skin conditioning and antioxidant protection. Aminopropyl ascorbyl phosphate is a form of Vitamin C that supports hyaluronic acid, increases skin smoothness and helps improve the appearance of dark patches. EGCG is a potent antioxidant found in green tea that provides antioxidant support while delivering soothing and calming benefits.

Any one of the compositions disclosed above and herein can be in the form of any pharmaceutically acceptable dosage form, including but not limited to, liquids, ointments, creams, oils, emulsions, lotions, gels, liquids, bioadhesive gels, sprays, shampoos, aerosols, pastes, foams, sunscreens, capsules, microcapsules, or in the form of an article or carrier, such as a bandage, insert, syringe-like applicator, pessary, powder, talc or other solid, shampoo, cleanser (leave on and wash off product), day creams, night creams, make-up removal creams, foundation creams, make-up removal formulations, protective or skin care body milks, skin care lotions, gels, or foams (such as cleansing or disinfecting lotions), bath compositions, deodorant compositions, aftershave and pre-shave gels or lotions, and agents that favor penetration within the epidermis, the dermis and keratin layers. The composition is capable of effectively treating, preventing, and/or minimizing the dermatological conditions described herein, without being systemically absorbed and without significantly irritating the skin.

In an exemplified embodiment, the composition is a topical composition comprising a naturally produced protein building block selected from adenosine, carnosine and arginine, and a stabilizing ingredient. An exemplary topical composition comprises arginine, carnosine, an adenosine, a skin firming agent, a skin hydration agent, a skin barrier agent, and an antioxidant. The exemplary composition achieves delivery of arginine into the skin; arginine is a precursor to nitric oxide and is processed in situ in the skin to generate nitric oxide on demand, i.e., in response to the local in situ need for nitric oxide. This topical composition uniquely supports and delivers arginine topically, where it contributes to a skin depot or an in situ reservoir of arginine. From the deport, skin enzymes access and deploy arginine to convert to nitric oxide on demand and as needed in the local environment.

Thus, the topical composition described herein supports the skin's natural process of nitric oxide creation and is supplemented with purposeful and targeted ingredients to address the specific needs of skin, and more particularly, the specific needs of skin in specific body areas, e.g., the skin of the neck. The topical composition is enhanced, optionally, with extracts, antioxidant systems and skin-supporting ingredients. In an embodiment, the composition comprises a firming complex that supports collagen to leave skin looking and feeling firmer and tighter and/or a skin barrier agent that supports the skin barrier to deliver supple, more youthful-looking skin.

III. Methods of Use

Methods for treating, preventing, and/or minimizing wrinkles, signs of aging skin, and/or skin imperfections are provided herein. Examples of signs of aging skin and/or skin imperfections which can be treated, prevented, and/or minimized with the compositions described herein, and the methods of use of the compositions, include, but are not limited to, (1) fine to moderate wrinkles, (2) liver spots or age spots (lentigines or solar lentigines), (3) uneven skin tone and/or texture, (4) sun-damaged skin or photodamaged skin (particularly UV radiation-induced oxidative stress), (5) blemishes, (6) hyperpigmented skin, (7) increased skin thickness, (8) dry skin, (9) loss of skin elasticity and collagen content, (10) melasmas (atypical pigmentation or hyper-pigmentation of the skin), (11) reduced skin clarity and/or radiance, (12) reduced skin smoothness and/or softness, (13) enlarged pore size (e.g., larger pore can make an individual appear older), (14) reduced hydration, (15) reduced skin tightness, and any combination thereof. Collectively the signs of aging skin, skin imperfections and scars are referred to as "dermatological conditions."

In an exemplary embodiment, a method for treating, reducing and/or minimizing dermatological conditions in a region of skin comprises applying a composition as described above and herein to the region of skin. In some embodiments, the composition is applied topically, which is a non-invasive administration technique. The composition can be applied to any skin region of a subject. In one embodiment, the composition is applied to the facial tissue of a subject. In another embodiment, the composition is applied to the neck tissue of a subject. It has been surprisingly found that the compositions of the present disclosure can be used to substantially treat, minimize, and/or diminish the dermatological conditions described above.

A method of treating skin is provided herein, which comprises providing any one of the compositions described above and herein, and applying or instructing to apply the composition to skin. In some embodiments, the composition may be applied to the skin once daily or twice daily. In some embodiments, the composition may be applied to the skin for a period of at least about 2 weeks or at least about 1 month. In some embodiments, the composition is applied to skin on a person's neck, décolleté, face, and/or back of hands. In some embodiments, the method of treating is a method of cosmetically treating. In some embodiments, the method of treating is a method of therapeutically (pharmaceutically) treating.

In any of the methods described above and herein, applying the composition to skin achieves a beneficial change in the skin. In certain embodiments, the beneficial change may be one or more of the following: a reduced appearance of fine lines or fine wrinkles, an improved appearance of sun damage, an improved appearance of skin firmness, an improved skin appearance, a perceived improvement in skin appearance, an improved evenness in skin tone, an improved hydration of skin, a reduction in redness, and/or an improved skin tone.

In any of the methods described above and herein, nitric oxide is produced or generated after application of the composition to skin, as evidenced by one or more of the following: an increased cutaneous blood flow in the treated skin region compared to cutaneous blood flow in a similar skin region not treated with the composition; an increased cutaneous blood flow in the treated skin region compared to cutaneous blood flow in a similar skin region treated with a composition identical in all respects except for the absence of one or more of arginine, adenosine, and/or carnosine; and/or an increased cutaneous blood flow in the treated skin region for a period of between about 2-48 hours, 2-36 hours, 2-24 hours, 2-12 hours or 2-8 hours after application to skin.

IV. Examples

The following examples are illustrative in nature and are in no way intended to be limiting.

Example 1

Exemplary Composition T-1

A topical composition, referred to herein as Composition T-1, in the form of an emulsion was prepared by creating an oil phase and a water phase, each with certain of the ingredients listed below. The oil phase was added to the water phase with stirring to create an oil in water emulsion.

Composition T-1 contained between about 0.1-1 wt % arginine, about 0.01-0.06 wt % adenosine, about 0.05-0.2 wt % carnosine, about 0.5-6 wt % niacinamide, and about 0.4-0.6 wt % of a magnesium ion source.

Composition T-1 also contained other ingredients, including, but not limited to, an emulsifier, a surfactant, a preservative, a gelling agent, a thickening agent, a skin firming agent, a skin hydration agent, a skin barrier agent, and an antioxidant. The other ingredients included one or more of the following: Ethylhexyl Olivate, Jojoba Esters, Glycerin, Cetearyl Olivate, Isocetyl Stearoyl Stearate, Sodium Lactate, Sorbitan Olivate, Coco-Caprylate/Caprate, Polyglycerin-6, Cetearyl Alcohol, Butylene Glycol, Cetyl Alcohol, Triheptanoin, Phenoxyethanol, Cetyl Palmitate, Linoleic Acid, Propanediol, Sorbitan Palmitate, Aminopropyl Ascorbyl Phosphate, Xanthan Gum, Ammonium Polyacryloyldimethyl Taurate, C9-12 Alkane, *Citrullus lanatus* (Watermelon) Fruit Extract, Polyurethane-100, Pentaerythrityl Tetra-di-t-butyl Hydroxyhydrocinnamate, Sodium Stearoyl Glutamate, Lens *Esculenta* (Lentil) Fruit Extract, Hydrolyzed *Eragrostis tef* Seed Extract, Hydrolyzed Sodium Hyaluronate, Tocopheryl Acetate, Linolenic Acid, Lecithin, *Sclerotium* Gum, *Pyrus malus* (Apple) Fruit Extract, Sorbitan Oleate, Squalane, Pullulan, Ethylhexylglycerin, Gluconolactone, *Tremella fuciformis* (Mushroom) Extract, Sodium Benzoate, Phytic Acid, Silica, Potassium Sorbate, Sodium PCA, Citric Acid, Heptapeptide-7, Tocopherol, Epigallocatechin Gallate, Myristyl Alcohol, Stearyl Alcohol, Calcium Gluconate, *Nicotiana benthamiana* Hexapeptide-40 sh-Polypeptide-76, and Sodium Hydroxide.

Example 2

Protein Analysis of Ex Vivo Skin Tissues and Nitric Oxide Availability

A study was conducted utilizing ex vivo skin tissues in order to investigate influence of the compositions of the present disclosure on protein expression or activity in tissues treated topically with the composition. The ex vivo tissues maintained a normal skin barrier function, a mature stratum corneum, a functional basal layer, all cell types and skin appendages of in vivo human skin.

Ex vivo skin tissues were obtained from donor and used for treatment and protein expression analysis within 72 hours of skin collection. Tissues were equilibrated in an incubator at 37° C., 5% $CO_2$, and ~95% humidity for two hours before applying the treatments. The equilibration medium was removed and replaced with 1.0 mL of maintenance media.

Following equilibration, 15 μL of the test topical composition of Example 1 (Composition T-1) was applied to the topical surface of each culture; a sterile glass spreader was used to distribute the composition across the surface. Each culture was visually inspected to ensure the even distribution of topical treatment. For the control group, 0.9% saline was used. Four tissue replicates (n=4) were included in each of the testing group ("Composition T-1") and control group ("Saline").

Following application of the test topical composition, the cultures were returned to 37° C. with 5% $CO_2$ for 24 hours. After the end of first day, treatment was removed using a cotton-swab soaked in phosphate buffered saline (PBS) and fresh composition was reapplied and the cultures were returned to 37° C. with 5% $CO_2$ for additional 24 hours.

After 48 hours of exposure, the topical composition was removed using a cotton-swab soaked in PBS. An 8 mm punch was taken of each sample to punch out the part of skin biopsy inside the silicon ring. Each skin biopsy was then cut in half, placed into tubes and snap frozen in liquid nitrogen to preserve the native state of enzymes and protein.

A standard assay was then performed to determine nitric oxide availability, which measured changes in target protein concentration using Enzyme-Linked Immunosorbent Assays (ELISAs) (e.g., Nitrate/Nitrite Colorimetric Assay (Cayman; Cat #780001)). A standard curve used to determine the concentration of test proteins is shown in FIG. 1. Statistical analysis was performed using a Student's t-test (unpaired t-test). Test groups with $p \leq 0.05$ were considered statistically significant.

Figure 2:
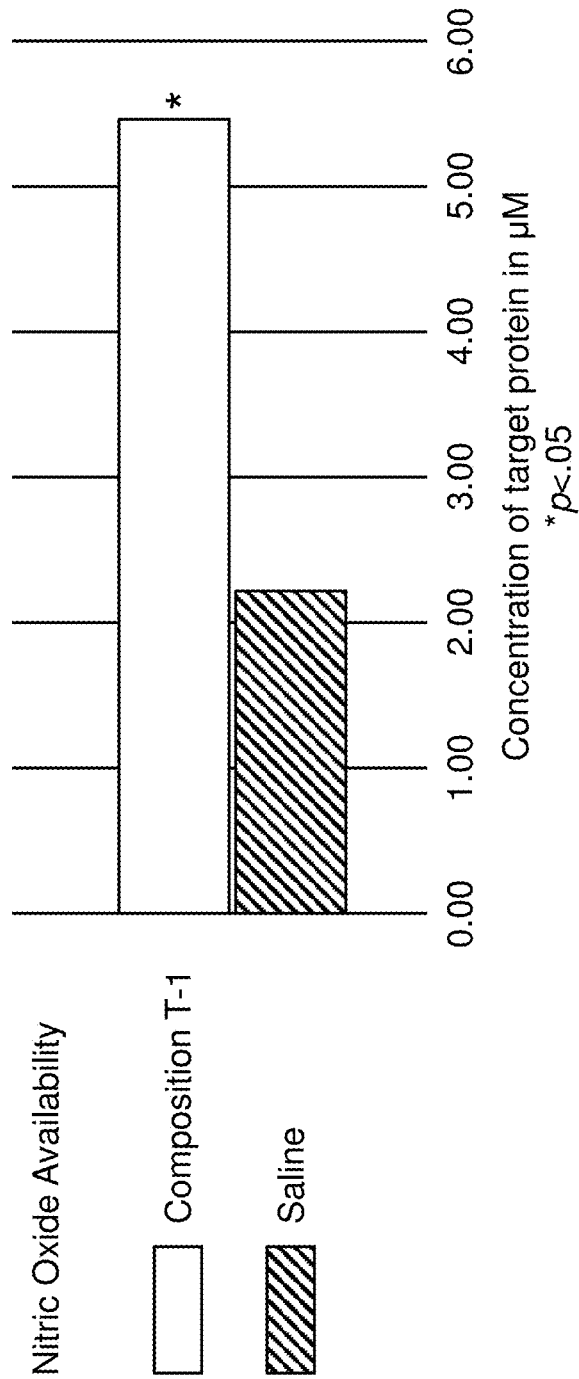
FIG. 2 illustrates increased nitric oxide availability to ex vivo skin tissue treated with an exemplary topical composition, Composition T-1.

The results show that more nitric oxide was present in ex vivo skin tissues that were treated with the test topical composition than in those that were treated with saline (see, FIG. 2). In fact, the availability of nitric oxide was increased by more than 200%. This suggests that test topical composition significantly increased nitric oxide availability when applied to ex vivo skin tissues.

Example 3

Evidence of Nitric Oxide Availability

Doppler ultrasound measurements were obtained to evaluate and visualize the difference in cutaneous blood flow in the neck between baseline (untreated control) and 2.5 hours following a single, thin layer application of the test topical composition (Composition T-1). Testing was conducted using LOGIQ E10 Ultrasound Series (GE Healthcare).

The results show an increased cutaneous blood flow in the neck skin treated with the test topical composition (see, FIG. 3B) compared to cutaneous blood flow in a similar skin region not treated with the composition (see, FIG. 3A).

Since youthful-acting skin cells require nitric oxide to open up nutrient and oxygen channels in the skin, the flow of nutrients and oxygen to skin cells is connected to dermal health and the body's natural healing process. The increased cutaneous blood flow in the neck skin treated with the test topical composition demonstrates the increased availability of nitric oxide in the treated neck skin.

Example 4

Efficacy and Tolerability Study

The efficacy and tolerability of twice-daily application of the test topical composition (Composition T-1) were evaluated in female subjects (n=26) of varying skin tones with mild-to-moderate lines/wrinkles on the neck. The evaluation was done in a clinical trial conducted by two Board-Certified dermatologists over the course of 12 weeks.

Figure 4:
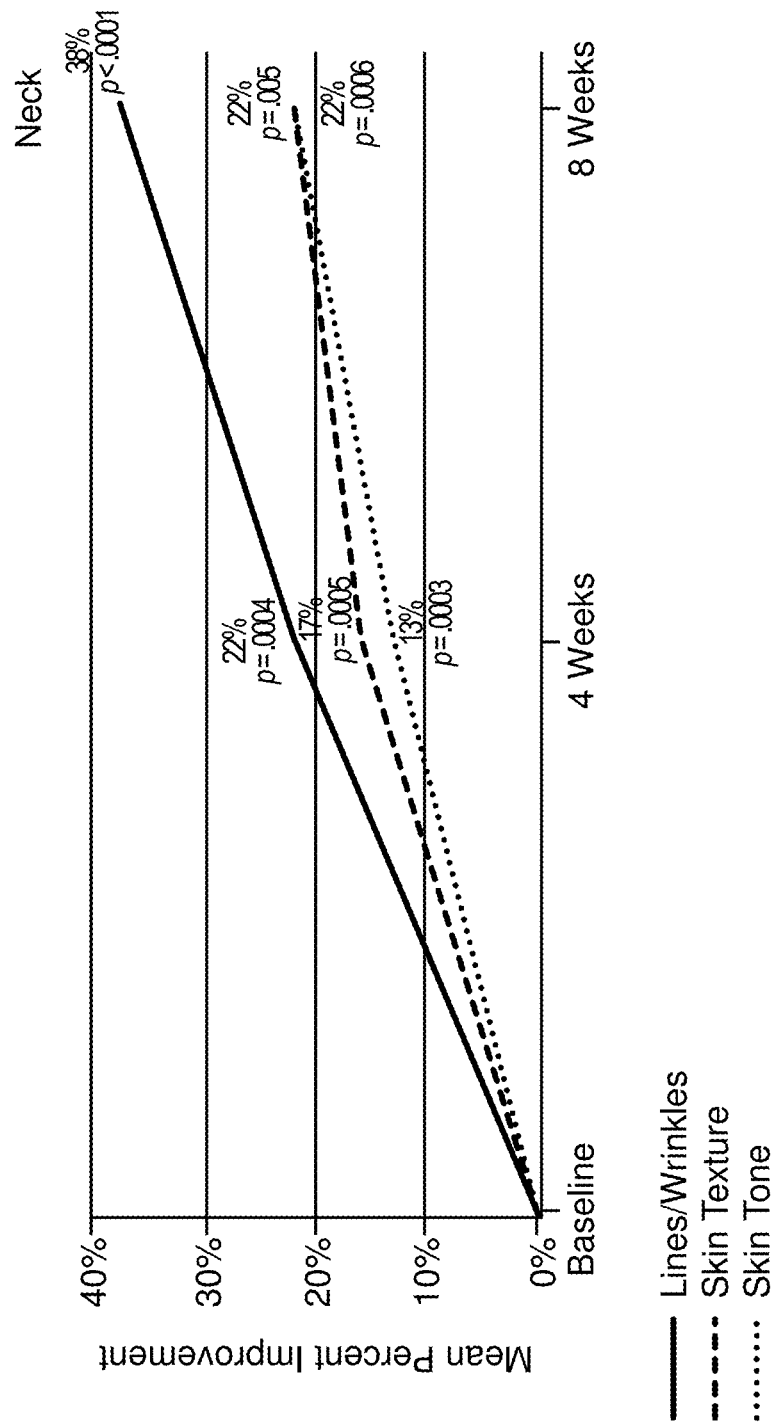
FIG. 4 illustrates mean percent improvement in appearance of key measurements of skin (lines/winkles, skin texture, and skin tone) over the course of 8 weeks following application of the exemplary topical composition T-1.

The subjects reported high levels of tolerability on the neck throughout the duration of the study. The results show early, statistically significant mean percent improvement in appearance of key measurements (e.g., lines/wrinkles, skin texture, and skin tone) at all timepoints (see, FIG. 4).

Exceptional subject satisfaction was reported after 8 weeks of use. 96% of subjects agreed that the skin on their neck looked firmer and tighter, and less crepey and saggy. They also felt their neck skin was more hydrated.

The results demonstrate that the test topical composition is effective in treating aging skin and improving appearance of the skin.

Example 5

Clinical Study of Combination Treatment

The efficacy and tolerability of twice-daily application of the test topical composition (Composition T-1) and nightly (PM) application of AlphaRet® Overnight Cream were evaluated in subjects (n=10) with mild-to-moderate lines/wrinkles on the neck and photodamage on the décolleté. The evaluation was done in a clinical trial conducted by two Board-Certified dermatologists over the course of 12 weeks.

Figure 5:
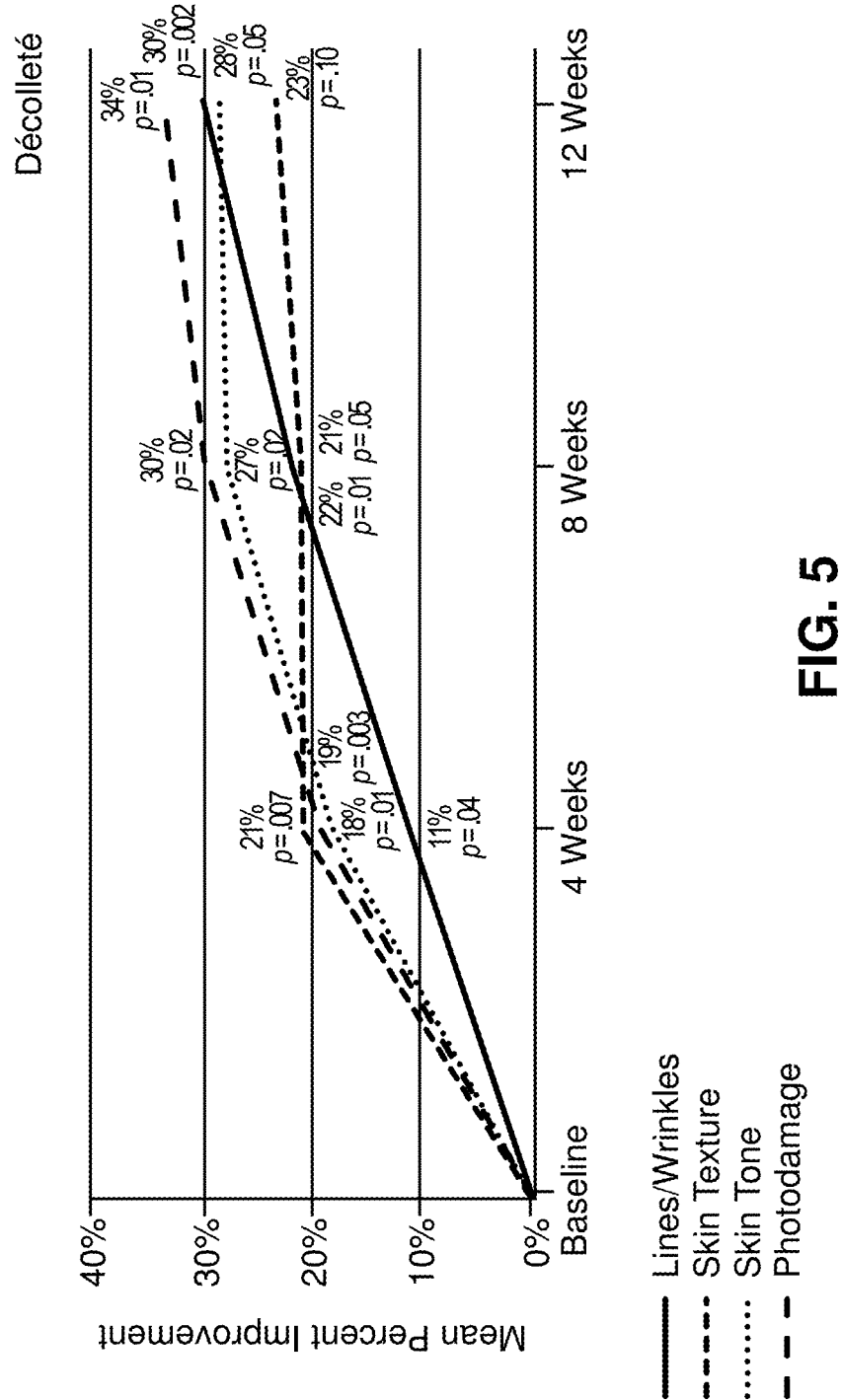
FIG. 5 illustrates mean percent improvement in appearance of key measurements of décolleté (lines/winkles, skin texture, skin tone, and photodamage) over the course of 12 weeks following application of the exemplary topical composition T-1 in the morning and evening in combination with application of AlphaRet® Overnight Cream in the evening.

The subjects reported high levels of tolerability of the combo on the neck and décolleté throughout the duration of the study. The results show statistically significant mean percent improvement in appearance of key measurements (lines/wrinkles, skin texture, skin tone, and photodamage) at all timepoints (see, FIG. 5).

Exceptional subject satisfaction was reported after 8 weeks of the combination use. 100% of subjects agreed that the skin on their neck looked smoother, brighter, and more even, and overall looked better. 100% of subjects agreed that the skin on their neck and décolleté looked firmer, tighter and brighter, and less crepey and saggy. They also felt their neck and décolleté skin was more hydrated.

Example 6

Exemplary Composition

An exemplary topical composition comprising the following ingredients was prepared: Aqua/Water, Niacinamide, Ethylhexyl Olivate, Jojoba Esters, Glycerin, Cetearyl Olivate, Isocetyl Stearoyl Stearate, Sodium Lactate, Sorbitan Olivate, Coco-Caprylate/Caprate, Polyglycerin-6, Cetearyl Alcohol, Butylene Glycol, Magnesium Gluconate, Arginine, Heptapeptide-7, *Nicotiana benthamiana* Hexapeptide-40 sh-Polypeptide-76, Hydrolyzed *Eragrostis tef* Seed Extract, Adenosine, Carnosine, Aminopropyl Ascorbyl Phosphate, *Citrullus lanatus* (Watermelon) Fruit Extract, Lens *Esculenta* (Lentil) Fruit Extract, Epigallocatechin Gallate, *Pyrus malus* (Apple) Fruit Extract, Hydrolyzed Sodium Hyaluronate, Linoleic Acid, Tocopheryl Acetate, Linolenic Acid, Squalane, Sodium PCA, *Tremella fuciformis* (Mushroom) Extract, Tocopherol, Cetyl Palmitate, Sorbitan Palmitate, Cetyl Alcohol, Pentaerythrityl Tetra-di-t-butyl Hydroxyhydrocinnamate, Sodium Stearoyl Glutamate, Propanediol, Silica, C9-12 Alkane, Pullulan, Xanthan Gum, Triheptanoin, *Sclerotium* Gum, Sorbitan Oleate, Ethylhexylglycerin, Ammonium Polyacryloyldimethyl Taurate, Myristyl Alcohol, Stearyl Alcohol, Calcium Gluconate, Polyurethane-100, Lecithin, Gluconolactone, Phenoxyethanol, Sodium Benzoate, Phytic Acid, Potassium Sorbate, Citric Acid, and Sodium Hydroxide.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A topical composition for treating ageing-related skin conditions, comprising:
    adenosine present from about 0.01 to about 0.5 wt %,
    arginine present from about 0.1 to about 1.0 wt %,
    carnosine present from about 0.05 to about 0.2 wt %,
    niacinamide present from about 0.5 to about 6 wt %, and
    a magnesium ion source present from about 0.1 to about 1.0 wt %,
    wherein upon application of the composition to a skin region, a nitric oxide is produced or generated and increases cutaneous blood flow in the skin region compared to cutaneous blood flow in a similar skin region not treated with the composition, as measured by doppler ultrasound, and
    wherein the composition is suitable for at least daily topical application to skin for a period of at least 32 days.

2. The composition of claim 1, wherein a weight ratio of the arginine to the adenosine is between about 10:1 and about 100:1, or wherein a weight ratio of the arginine to the adenosine is about 25:1.

3. The composition of claim 1, wherein a weight ratio of the arginine to the carnosine is between about 2:1 and about 20:1, or wherein a weight ratio of the arginine to the carnosine is about 5:1.

4. The composition of claim 1, wherein a weight ratio of the arginine to the carnosine is about 5:1 and a weight ratio of the arginine to the adenosine is about 25:1.

5. The composition of claim 1, wherein the composition comprises:
    about 0.01-0.06 wt % of the adenosine;
    about 1.5-6 wt % of the niacinamide; and
    a magnesium ion source present from about 0.4 to about 0.6 wt %,
    wherein a weight ratio of the arginine to the carnosine is about 5:1 and a weight ratio of the arginine to the adenosine is about 25:1.

6. The composition of claim 1, further comprising epigallocatechin gallate.

7. The composition of claim 1, wherein the arginine is L-arginine.

8. The composition of claim 1, wherein the magnesium ion source is a magnesium salt.

9. The composition of claim 8, wherein the magnesium salt is selected from the group consisting of magnesium gluconate, magnesium glycinate, magnesium citrate, magnesium carbonate, magnesium malate, magnesium taurate, magnesium hydroxide, magnesium sulfate, magnesium hydroxide, and magnesium oxide.

10. The composition of claim 1, further comprising an extracellular matrix component.

11. The composition of claim 10, wherein the extracellular matrix component is selected from the group consisting of collagen, elastin, fibronectin, hyaluronic acid, sodium hyaluronate, and lectin.

12. The composition of claim 11, wherein the extracellular matrix component has an average molecular weight of between about 1,000-60,000 daltons.

13. A topical composition for treating ageing-related skin conditions, comprising:
    about 0.1 to about 1 wt % arginine;
    about 0.05 to about 0.2 wt % carnosine;
    about 0.01 to about 0.06 wt % an adenosine;
    a skin firming agent comprising about 0.4 to about 0.6 wt % of a magnesium ion source;

a skin hydration agent comprising about 0.5 to about 6 wt % niacinamide;
a skin barrier agent; and
an antioxidant,
wherein upon application of the composition to a skin region, a nitric oxide is produced or generated and increases cutaneous blood flow in the skin region compared to cutaneous blood flow in a similar skin region not treated with the composition, as measured by doppler ultrasound, and
wherein the composition is suitable for at least daily topical application to skin for a period of at least 32 days.

14. The composition of claim 13, wherein a weight ratio of the arginine to the carnosine is about 5:1 and a weight ratio of the arginine to the adenosine is about 25:1.

15. The composition of claim 13, wherein a weight ratio of the arginine to the adenosine is between about 10:1 and about 100:1 or between about 15:1 and about 50:1.

16. The composition of claim 13, wherein a weight ratio of the arginine to the carnosine is between about 2:1 and 20:1 or between about 2:1 and about 10:1.

17. The composition of claim 13, wherein the skin firming agent is selected from the group consisting of heptapeptide-7, magnesium gluconate, *Nicotiana benthamiana* hexapeptide-40sh-polypeptide-76, and hydrolyzed *Eragrostis tef* seed extract.

18. The composition of claim 13, wherein the skin hydration agent is selected from the group consisting of fruit extract complex, hydrolyzed sodium hyaluronate, and jojoba esters.

19. The composition of claim 13, wherein the skin barrier agent is selected from the group consisting of jojoba esters, linoleic acid, linolenic acid, and squalane.

20. The composition of claim 13, wherein the antioxidant is selected from the group consisting of tocopheryl acetate, aminopropyl ascorbyl phosphate, and epigallocatechin gallate.

21. A method for treating ageing-related skin conditions, comprising:
providing the composition according to claim 1; and
applying or instructing to apply the composition to a skin region,
wherein the age-related skin conditions include age spots, sun damage, blemishes, hyperpigmented skin, age spots, increased skin thickness, loss of skin elasticity and collagen content, dry skin, lentigines, melasma and/or scars,
wherein upon application of the composition to the skin region, a nitric oxide is produced or generated and increases cutaneous blood flow in the skin region compared to cutaneous blood flow in a similar skin region not treated with the composition, as measured by doppler ultrasound, and
wherein the composition is suitable for at least daily topical application to skin for a period of at least 32 days.

22. The composition of claim 1, wherein the composition comprises Aqua/Water, Ethylhexyl Olivate, Jojoba Esters, Glycerin, Cetearyl Olivate, Isocetyl Stearoyl Stearate, Sodium Lactate, Sorbitan Olivate, Coco-Caprylate/Caprate, Polyglycerin-6, Cetearyl Alcohol, Butylene Glycol, Magnesium Gluconate, Heptapeptide-7, *Nicotiana benthamiana* Hexapeptide-40 sh-Polypeptide-76, Hydrolyzed *Eragrostis tef* Seed Extract, Aminopropyl Ascorbyl Phosphate, *Citrullus lanatus* (Watermelon) Fruit Extract, Lens *Esculenta* (Lentil) Fruit Extract, Epigallocatechin Gallate, *Pyrus malus* (Apple) Fruit Extract, Hydrolyzed Sodium Hyaluronate, Linoleic Acid, Tocopheryl Acetate, Linolenic Acid, Squalane, Sodium PCA, *Tremella fuciformis* (Mushroom) Extract, Tocopherol, Cetyl Palmitate, Sorbitan Palmitate, Cetyl Alcohol, Pentaerythrityl Tetra-di-t-butyl Hydroxyhydrocinnamate, Sodium Stearoyl Glutamate, Propanediol, Silica, C9-12 Alkane, Pullulan, Xanthan Gum, Triheptanoin, *Sclerotium* Gum, Sorbitan Oleate, Ethylhexylglycerin, Ammonium Polyacryloyldimethyl Taurate, Myristyl Alcohol, Stearyl Alcohol, Calcium Gluconate, Polyurethane-100, Lecithin, Gluconolactone, Phenoxyethanol, Sodium Benzoate, Phytic Acid, Potassium Sorbate, Citric Acid, and Sodium Hydroxide.

23. The composition of claim 13, wherein the composition comprises Aqua/Water, Ethylhexyl Olivate, Jojoba Esters, Glycerin, Cetearyl Olivate, Isocetyl Stearoyl Stearate, Sodium Lactate, Sorbitan Olivate, Coco-Caprylate/Caprate, Polyglycerin-6, Cetearyl Alcohol, Butylene Glycol, Magnesium Gluconate, Heptapeptide-7, *Nicotiana benthamiana* Hexapeptide-40 sh-Polypeptide-76, Hydrolyzed *Eragrostis tef* Seed Extract, Aminopropyl Ascorbyl Phosphate, *Citrullus lanatus* (Watermelon) Fruit Extract, Lens *Esculenta* (Lentil) Fruit Extract, Epigallocatechin Gallate, *Pyrus malus* (Apple) Fruit Extract, Hydrolyzed Sodium Hyaluronate, Linoleic Acid, Tocopheryl Acetate, Linolenic Acid, Squalane, Sodium PCA, *Tremella fuciformis* (Mushroom) Extract, Tocopherol, Cetyl Palmitate, Sorbitan Palmitate, Cetyl Alcohol, Pentaerythrityl Tetra-di-t-butyl Hydroxyhydrocinnamate, Sodium Stearoyl Glutamate, Propanediol, Silica, C9-12 Alkane, Pullulan, Xanthan Gum, Triheptanoin, *Sclerotium* Gum, Sorbitan Oleate, Ethylhexylglycerin, Ammonium Polyacryloyldimethyl Taurate, Myristyl Alcohol, Stearyl Alcohol, Calcium Gluconate, Polyurethane-100, Lecithin, Gluconolactone, Phenoxyethanol, Sodium Benzoate, Phytic Acid, Potassium Sorbate, Citric Acid, and Sodium Hydroxide.

24. The method of claim 21, wherein the composition comprises Aqua/Water, Ethylhexyl Olivate, Jojoba Esters, Glycerin, Cetearyl Olivate, Isocetyl Stearoyl Stearate, Sodium Lactate, Sorbitan Olivate, Coco-Caprylate/Caprate, Polyglycerin-6, Cetearyl Alcohol, Butylene Glycol, Magnesium Gluconate, Heptapeptide-7, *Nicotiana benthamiana* Hexapeptide-40 sh-Polypeptide-76, Hydrolyzed *Eragrostis tef* Seed Extract, Aminopropyl Ascorbyl Phosphate, *Citrullus lanatus* (Watermelon) Fruit Extract, Lens *Esculenta* (Lentil) Fruit Extract, Epigallocatechin Gallate, *Pyrus malus* (Apple) Fruit Extract, Hydrolyzed Sodium Hyaluronate, Linoleic Acid, Tocopheryl Acetate, Linolenic Acid, Squalane, Sodium PCA, *Tremella fuciformis* (Mushroom) Extract, Tocopherol, Cetyl Palmitate, Sorbitan Palmitate, Cetyl Alcohol, Pentaerythrityl Tetra-di-t-butyl Hydroxyhydrocinnamate, Sodium Stearoyl Glutamate, Propanediol, Silica, C9-12 Alkane, Pullulan, Xanthan Gum, Triheptanoin, *Sclerotium* Gum, Sorbitan Oleate, Ethylhexylglycerin, Ammonium Polyacryloyldimethyl Taurate, Myristyl Alcohol, Stearyl Alcohol, Calcium Gluconate, Polyurethane-100, Lecithin, Gluconolactone, Phenoxyethanol, Sodium Benzoate, Phytic Acid, Potassium Sorbate, Citric Acid, and Sodium Hydroxide.

* * * * *